(12) United States Patent
Eitan et al.

(10) Patent No.: US 11,191,897 B2
(45) Date of Patent: Dec. 7, 2021

(54) IN CYCLE PRESSURE MEASUREMENT

(71) Applicant: EITAN MEDICAL LTD., Netanya (IL)

(72) Inventors: Boaz Eitan, Hofit (IL); Amir Rasowsky, Yakir (IL); David Mizrahi, Jerusalem (IL)

(73) Assignee: EITAN MEDICAL LTD., Netanya (IL)

( * ) Notice: Subject to any disclaimer, the term of this patent is extended or adjusted under 35 U.S.C. 154(b) by 80 days.

(21) Appl. No.: 16/808,652

(22) Filed: Mar. 4, 2020

(65) Prior Publication Data
US 2020/0282138 A1 Sep. 10, 2020

Related U.S. Application Data

(60) Provisional application No. 62/813,292, filed on Mar. 4, 2019.

(51) Int. Cl.
*A61M 5/168* (2006.01)
*A61M 5/142* (2006.01)
*G01L 19/00* (2006.01)

(52) U.S. Cl.
CPC ........ *A61M 5/16859* (2013.01); *A61M 5/142* (2013.01); *A61M 5/16813* (2013.01); *G01L 19/00* (2013.01); *A61M 2205/3331* (2013.01)

(58) Field of Classification Search
CPC ...... A61M 2205/33; A61M 2205/3362; A61M 5/14; A61M 5/168; A61M 5/16831;
(Continued)

(56) References Cited

U.S. PATENT DOCUMENTS

| 3,379,950 A | 4/1968 | Friedline |
| 3,993,061 A | 11/1976 | O'Leary |

(Continued)

FOREIGN PATENT DOCUMENTS

| CN | 103727021 | 4/2014 |
| EP | 1381843 | 3/2009 |

(Continued)

OTHER PUBLICATIONS

European Search Repod dated May 12, 2021 which issued during the prosecution of Applicant's European App No. 20212979.7.
(Continued)

*Primary Examiner* — Jason E Flick
(74) *Attorney, Agent, or Firm* — The Roy Gross Law Firm, LLC; Roy Gross

(57) ABSTRACT

An infusion pump includes inlet and outlet valves and a squeezing element configured to squeeze a fluid line coupled to the infusion pump. A method includes at least one round of valve operation check prior to initiation of a delivery session of fluid to a subject, and subsequently, after an intake phase and before a delivery phase of at least one infusion pump cycle, determining for the at least one pump cycle, an absolute amount of air in the fluid line. The valve operation check and the determining of the amount of air each include: (A) closing the inlet valve to confine a section of the fluid line between the inlet and outlet valves; (B) squeezing the confined section; (C) measuring the pressure within the confined section; and (D) subsequently, relieving the pressure in the confined section. Other applications are also described.

14 Claims, 6 Drawing Sheets

(58) Field of Classification Search
CPC ...... A61M 5/16854; A61M 2205/3331; A61M 5/142; A61M 5/16813; A61M 5/16859; A61M 2005/14208; A61M 5/365; G01L 19/00; G01L 7/00
See application file for complete search history.

(56) References Cited

U.S. PATENT DOCUMENTS

| | | |
|---|---|---|
| 4,236,880 A | 12/1980 | Archibald |
| 4,322,668 A | 3/1982 | Trussler et al. |
| 4,391,600 A | 7/1983 | Archibald |
| 4,650,469 A | 3/1987 | Berg et al. |
| 5,018,945 A | 5/1991 | D'Silva |
| 5,049,047 A | 9/1991 | Polaschegg et al. |
| 5,096,385 A | 3/1992 | Georgi et al. |
| 5,116,203 A | 5/1992 | Natwick et al. |
| 5,340,951 A | 8/1994 | Hungerbühler et al. |
| 5,439,355 A | 8/1995 | Jimison et al. |
| 5,450,847 A | 10/1995 | Kampfe et al. |
| 5,807,075 A | 9/1998 | Jacobsen et al. |
| 5,807,322 A | 9/1998 | Lindsey et al. |
| 5,843,035 A | 12/1998 | Bowman et al. |
| 6,312,227 B1 | 11/2001 | Davis |
| 6,494,864 B1 | 12/2002 | Kerwin et al. |
| 6,523,414 B1 | 2/2003 | Malmstrom et al. |
| 6,531,708 B1 | 3/2003 | Malmstrom et al. |
| 6,554,806 B2 | 4/2003 | Butterfield et al. |
| 6,659,976 B2 | 12/2003 | Beck et al. |
| 6,679,862 B2 | 1/2004 | Diaz et al. |
| 6,702,779 B2 | 3/2004 | Connelly et al. |
| 6,750,468 B2 | 6/2004 | Malmstrom et al. |
| 6,852,094 B2 | 2/2005 | Beck et al. |
| 6,889,556 B2 | 5/2005 | Steger |
| 6,907,788 B2 | 6/2005 | Malmstrom et al. |
| 6,908,452 B2 | 6/2005 | Diaz et al. |
| 6,979,311 B2 | 12/2005 | Miles et al. |
| 7,048,715 B2 | 5/2006 | Diaz et al. |
| 7,059,840 B2 | 6/2006 | Corwin et al. |
| 7,070,575 B2 | 7/2006 | Beck et al. |
| 7,092,796 B2 | 8/2006 | Vanderveen |
| 7,121,143 B2 | 10/2006 | Malmstrom et al. |
| 7,163,381 B1 | 1/2007 | Barak |
| 7,356,382 B2 | 4/2008 | Vanderveen |
| 7,384,408 B2 | 6/2008 | Barak |
| 7,497,842 B2 | 3/2009 | Diaz et al. |
| 7,695,448 B2 | 4/2010 | Cassidy et al. |
| 7,726,174 B2 | 6/2010 | Riley et al. |
| 7,758,551 B2 | 7/2010 | Wiesner et al. |
| 7,819,838 B2 | 10/2010 | Ziegler et al. |
| 7,875,004 B2 | 1/2011 | Yodfat et al. |
| 7,881,883 B2 | 2/2011 | Remde |
| 7,892,199 B2 | 2/2011 | Mhatre et al. |
| 7,896,197 B2 | 3/2011 | Furey et al. |
| 7,921,718 B2 | 4/2011 | Malmstrom et al. |
| 7,922,700 B2 | 4/2011 | Evans et al. |
| 7,967,773 B2 | 6/2011 | Amborn et al. |
| 7,981,082 B2 | 7/2011 | Wang et al. |
| 8,025,654 B2 | 9/2011 | Barak |
| 8,034,020 B2 | 10/2011 | Dewey |
| 8,048,022 B2 | 11/2011 | Moy et al. |
| 8,081,069 B2 | 12/2011 | Haueter et al. |
| 8,105,269 B2 | 1/2012 | Zhou |
| 8,142,400 B2 | 3/2012 | Rotem et al. |
| 8,152,780 B2 | 4/2012 | Evans et al. |
| 8,167,832 B2 | 5/2012 | Bowman et al. |
| 8,182,461 B2 | 5/2012 | Pope et al. |
| 8,225,639 B2 | 7/2012 | Riley et al. |
| 8,232,484 B2 | 7/2012 | Hauck |
| 8,286,505 B2 | 10/2012 | Wade |
| 8,287,495 B2 | 10/2012 | Michaud et al. |
| 8,298,184 B2 | 10/2012 | Diperna et al. |
| 8,328,786 B2 | 12/2012 | Strickler et al. |
| 8,343,111 B2 | 1/2013 | Beck et al. |
| 8,361,021 B2 | 1/2013 | Wang et al. |
| 8,378,837 B2 | 2/2013 | Wang et al. |
| 8,394,051 B2 | 3/2013 | Geipel |
| 8,419,676 B2 | 4/2013 | Evans et al. |
| 8,448,523 B2 | 5/2013 | Richter |
| 8,486,005 B2 | 7/2013 | Yodfat et al. |
| 8,486,020 B2 | 7/2013 | Hills et al. |
| 8,496,613 B2 | 7/2013 | Zhou |
| 8,539,672 B2 | 9/2013 | Eggers et al. |
| 8,567,235 B2 | 10/2013 | Bojan et al. |
| 8,641,671 B2 | 2/2014 | Michaud et al. |
| 8,657,778 B2 | 2/2014 | Ziegler et al. |
| 8,690,014 B2 | 4/2014 | Haueter et al. |
| 8,690,860 B2 | 4/2014 | Abal |
| 8,733,178 B2 | 5/2014 | Bivans et al. |
| 8,752,436 B2 | 6/2014 | Beck et al. |
| 8,758,323 B2 | 6/2014 | Michaud et al. |
| 8,771,227 B2 | 7/2014 | Connelly et al. |
| 8,795,225 B2 | 8/2014 | Lewis et al. |
| 8,808,230 B2 | 8/2014 | Rotstein |
| 8,821,432 B2 | 9/2014 | Unverdorben |
| 8,852,141 B2 | 10/2014 | Mhatre et al. |
| 8,859,972 B2 | 10/2014 | Cummings et al. |
| 8,876,787 B2 | 11/2014 | Beck et al. |
| 8,900,213 B2 | 12/2014 | Pope et al. |
| 8,926,561 B2 | 1/2015 | Verhoef et al. |
| 8,943,894 B2 | 2/2015 | Geipel |
| 8,945,064 B2 | 2/2015 | Gravesen et al. |
| 8,961,453 B2 | 2/2015 | Bowman et al. |
| 8,974,415 B2 | 3/2015 | Robert et al. |
| 8,986,253 B2 | 3/2015 | Diperna et al. |
| 9,004,886 B2 | 4/2015 | Beck et al. |
| 9,005,153 B2 | 4/2015 | Kopperschmidt et al. |
| 9,017,296 B2 | 4/2015 | Beck et al. |
| 9,033,923 B2 | 5/2015 | Hartman et al. |
| 9,101,712 B2 | 8/2015 | Denis et al. |
| 9,109,966 B2 | 8/2015 | Duits |
| 9,132,230 B2 | 9/2015 | Blomquist |
| 9,162,023 B2 | 10/2015 | Barnes et al. |
| 9,173,998 B2 | 11/2015 | Rosinko et al. |
| 9,211,377 B2 | 12/2015 | Diperna et al. |
| 9,227,008 B2 | 1/2016 | Magnenat et al. |
| 9,234,850 B2 | 1/2016 | Hammond et al. |
| 9,248,230 B2 | 2/2016 | Geipel et al. |
| 9,272,087 B2 | 3/2016 | Halbert et al. |
| 9,285,324 B2 | 3/2016 | Leuenberger Jockel |
| 9,308,323 B2 | 4/2016 | Adams |
| 9,375,531 B2 | 6/2016 | Lee et al. |
| 9,408,968 B2 | 8/2016 | Browne et al. |
| 9,415,158 B2 | 8/2016 | Miller et al. |
| 9,427,521 B2 | 8/2016 | Pope et al. |
| 9,468,713 B2 | 10/2016 | Hoenninger, III et al. |
| 9,474,854 B2 | 10/2016 | Mhatre et al. |
| 9,480,793 B2 | 11/2016 | Mhatre et al. |
| 9,480,794 B2 | 11/2016 | Keith et al. |
| 9,545,478 B2 | 1/2017 | Abal |
| 9,561,323 B2 | 2/2017 | Plahey et al. |
| 9,603,998 B2 | 3/2017 | Geipel et al. |
| 9,610,404 B2 | 4/2017 | Rotstein |
| 9,642,777 B2 | 5/2017 | Lewis et al. |
| 9,662,437 B2 | 5/2017 | Moosai |
| 9,675,756 B2 | 6/2017 | Kamen et al. |
| 9,677,555 B2 | 6/2017 | Kamen et al. |
| 9,682,192 B2 | 6/2017 | Marsh et al. |
| 9,683,562 B2 | 6/2017 | Davis et al. |
| 9,717,849 B2 | 8/2017 | Mhatre et al. |
| 9,757,517 B2 | 9/2017 | Eberhard |
| 9,770,552 B2 | 9/2017 | Hartman et al. |
| 9,775,947 B2 | 10/2017 | Keith et al. |
| 9,789,251 B2 | 10/2017 | Robert et al. |
| 9,839,744 B2 | 12/2017 | Muto et al. |
| 9,879,668 B2 | 1/2018 | Yavorsky et al. |
| 9,901,676 B2 | 2/2018 | Mijers et al. |
| 9,932,977 B2 | 4/2018 | Bresina et al. |
| 9,937,290 B2 | 4/2018 | Connelly et al. |
| 9,937,291 B2 | 4/2018 | Eberhard |
| 9,958,344 B2 | 5/2018 | Burkhard |
| 9,962,486 B2 | 5/2018 | Rosinko et al. |
| 9,987,424 B2 | 6/2018 | Kim |
| 9,995,642 B2 | 6/2018 | Shimoyama et al. |
| 10,004,847 B2 | 6/2018 | Wander et al. |

(56) References Cited

U.S. PATENT DOCUMENTS

| | | |
|---|---|---|
| 10,006,453 B2 | 6/2018 | Girard et al. |
| 10,022,494 B2 | 7/2018 | Shimizu |
| 10,022,495 B2 | 7/2018 | Halbert et al. |
| 10,022,496 B2 | 7/2018 | Geipel et al. |
| 10,046,112 B2 | 8/2018 | Oruklu et al. |
| 10,080,836 B2 | 9/2018 | Juretich et al. |
| 10,092,697 B2 | 10/2018 | Nessel et al. |
| 10,112,009 B2 | 10/2018 | Dudar et al. |
| 10,151,646 B2 | 12/2018 | Heo et al. |
| 10,539,453 B2 | 1/2020 | Hauck |
| 2003/0141468 A1 | 7/2003 | Malmstrom et al. |
| 2004/0013538 A1 | 1/2004 | Fuchs |
| 2005/0107923 A1 | 5/2005 | Vanderveen |
| 2005/0147508 A1 | 7/2005 | Luongo et al. |
| 2006/0173412 A1 | 8/2006 | Susi |
| 2006/0189926 A1 | 8/2006 | Hall et al. |
| 2006/0206054 A1* | 9/2006 | Shekalim ............... A61M 5/141 604/122 |
| 2007/0123781 A1 | 5/2007 | Callahan et al. |
| 2007/0179435 A1 | 8/2007 | Braig et al. |
| 2008/0283296 A1 | 11/2008 | Zamora et al. |
| 2009/0240201 A1 | 9/2009 | Rotem et al. |
| 2009/0293588 A1 | 12/2009 | Riley et al. |
| 2010/0106082 A1* | 4/2010 | Zhou ................. A61M 5/14232 604/67 |
| 2010/0114001 A1 | 5/2010 | O'Mahony |
| 2010/0212407 A1 | 8/2010 | Stringham et al. |
| 2010/0280446 A1 | 11/2010 | Kalpin |
| 2011/0087165 A1 | 4/2011 | Amborn et al. |
| 2011/0152772 A1 | 6/2011 | Rotem et al. |
| 2011/0190606 A1 | 8/2011 | Gable et al. |
| 2012/0053562 A1 | 3/2012 | Haase |
| 2012/0205312 A1 | 8/2012 | Hogard |
| 2012/0238949 A1 | 9/2012 | Kalpin |
| 2012/0330574 A1 | 12/2012 | Ruiter et al. |
| 2013/0035659 A1 | 2/2013 | Hungerford et al. |
| 2013/0226129 A1 | 8/2013 | Unverdorben |
| 2013/0336814 A1 | 12/2013 | Kamen et al. |
| 2014/0066850 A1 | 3/2014 | Robert et al. |
| 2014/0119954 A1 | 5/2014 | Schweitzer et al. |
| 2014/0121639 A1 | 5/2014 | Lowery et al. |
| 2014/0228755 A1 | 8/2014 | Darrah et al. |
| 2015/0029816 A1 | 1/2015 | Beyer et al. |
| 2015/0238689 A1 | 8/2015 | Shimizu |
| 2015/0367120 A1 | 12/2015 | Kusters et al. |
| 2016/0177937 A1 | 6/2016 | Liu et al. |
| 2018/0140770 A1 | 5/2018 | Hetchler et al. |
| 2018/0200456 A1 | 7/2018 | Eitan et al. |
| 2018/0318505 A1 | 11/2018 | Eitan et al. |

FOREIGN PATENT DOCUMENTS

| | | |
|---|---|---|
| EP | 2040056 | 9/2010 |
| EP | 1381889 | 3/2016 |
| EP | 2570826 | 8/2016 |
| FR | 2553151 A1 | 4/1985 |
| GB | 2150644 A | 7/1985 |
| WO | 02/068018 | 9/2002 |
| WO | 2012/126744 A1 | 9/2012 |
| WO | 2019155453 | 8/2019 |
| WO | 2020/178824 A1 | 9/2020 |

OTHER PUBLICATIONS

European Search Report, European Application No. 20160966.6, dated Jun. 4, 2020.
U.S. Office Action, U.S. Appl. No. 15/740,365, dated Jun. 22, 2020.
International Search Report, International Application No. PCT/IL2018/050409, dated Aug. 5, 2018.
European Search Report, European Application No. 16817348, dated Jun. 3, 2019.
USPTO Office Action for U.S. Appl. No. 16/462,458, dated Aug. 3, 2021, 23 pp.
Extended European Search Report for European Application No. 18905766.4, dated Oct. 8, 2021, 8pp.

* cited by examiner

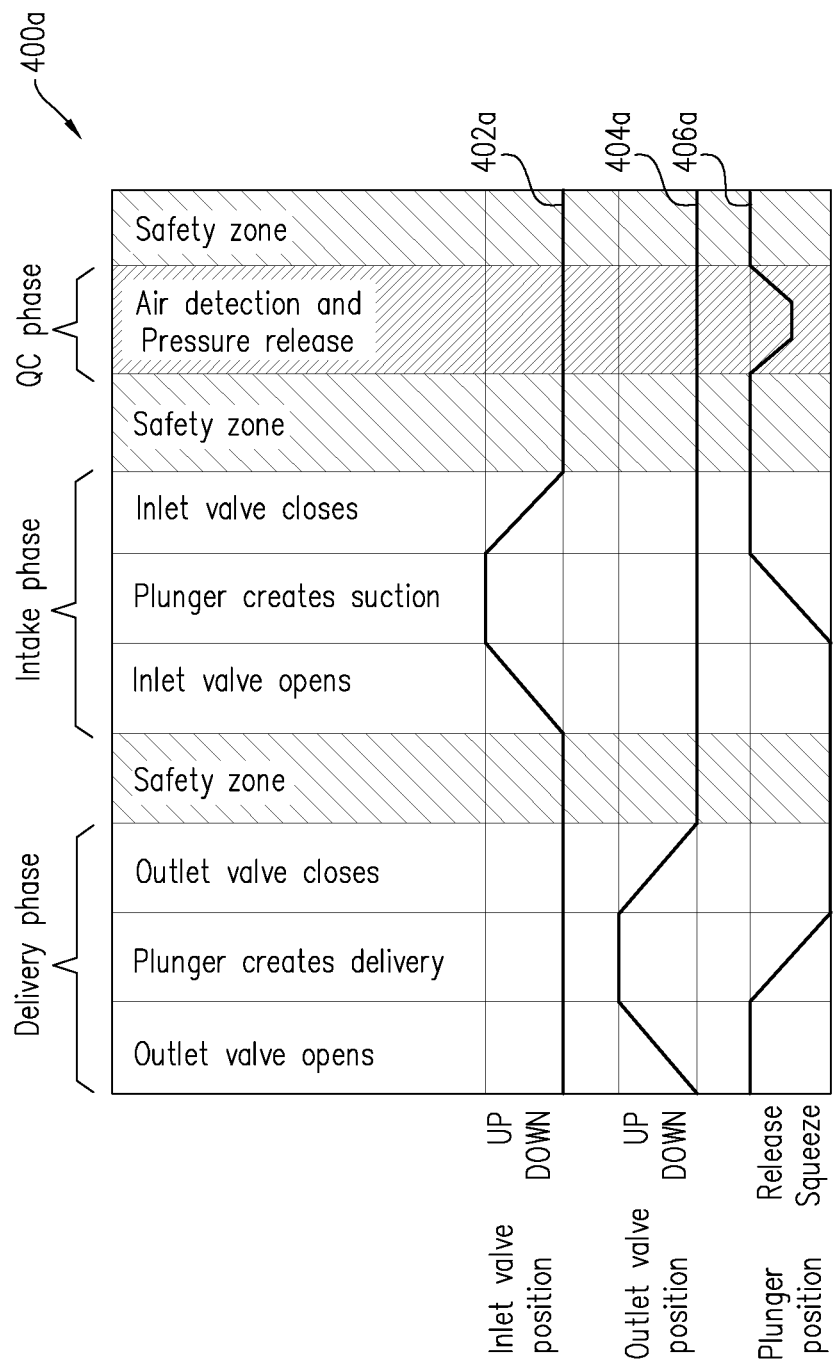

IN CYCLE PRESSURE MEASUREMENT

CROSS-REFERENCE TO RELATED APPLICATIONS

This application is a Non-Provisional under 35 USC 111(a) which claims the benefit of and priority to U.S. Provisional Application No. 62/813,292 to Eitan et al., filed Mar. 4, 2019 entitled, "IN CYCLE PRESSURE MEASUREMENT," which is incorporated herein by reference in its entirety.

FIELD OF THE INVENTION

The present invention relates generally to the field of measuring air in a fluid line and quality of the tube engagement to a pump.

BACKGROUND OF THE INVENTION

Modern medicine uses many automated fluid delivery systems and devices to administer medications, from saline to chemotherapy. The delivery of medications may result in an undesired delivery of air into the patient. Air embolism is a known undesired result of air injection into the patient. In some pumps, before starting operation, the quality of the set engagement is tested by a special operating mode where both proximal and distal valves are closed and pressure is created in the tube between the valves. However, such measurement cannot be performed during infusion pump operation.

During pump operation, typical pumps cycle between an intake phase, during which an infusion fluid is taken in from a fluid reservoir, such as an infusion fluid bag or syringe, and a delivery phase during which the fluid is delivered to the patient. A total delivery session typically includes numerous infusion cycles.

Some infusion pumps include dedicated components designed to detect an occlusion in the line and separate dedicated components for detecting and monitoring an amount of air or gas in the line, which may be inadvertently delivered to a patient while infusing the desired fluid.

SUMMARY OF THE INVENTION

The present disclosure is directed to an infusion pump in which measuring the pressure and air detection are combined into one detector. The air detection is done during an infusion pump cycle by creating pressure in the infusion tube during a special mode of operation in each cycle.

In general, the present disclosure relates to infusion pumps including an inlet valve configured to regulate the flow from an infusion fluid reservoir to an infusion fluid line, an outlet valve configured to regulate flow from the infusion fluid line to a patient, and a squeezing element, e.g., a plunger, configured to squeeze the infusion fluid line, thereby causing infusion fluid flow to the patient.

During operation the infusion pump repetitively cycles through infusion pump cycles, which each include an intake phase for intake of infusion fluid from an infusion fluid reservoir and a delivery phase for delivery of the infusion fluid to a patient. During the intake phase of the infusion pump cycle, the inlet valve of the infusion pump is opened (while the outlet valve is closed), and the plunger is raised to an upper position thereby creating a suction force that causes infusion fluid intake. Once the required amount of infusion fluid has been taken in, the inlet valve is closed (while the outlet valve remains closed) and the intake phase completed. During the delivery phase, the outlet valve is opened and the plunger lowered to squeeze the infusion fluid line to cause delivery of the infusion fluid to the patient. Once the delivery has been completed, the outlet valve is closed, and the delivery phase completed. Typically, upon completion of the delivery phase, a subsequent intake phase (of a subsequent infusion pump cycle) is commenced.

For some applications, valve function and/or proper priming of the fluid line may be determined prior to commencing a delivery session, i.e., after engagement of the infusion set to the pump or after priming of the fluid line by the pump. Prior to delivery initiation, the section of the infusion fluid line, confined by the inlet and the outlet valves, may be squeezed by the plunger and the pressure within the confined section measured by the pressure sensor, followed by the pressure release. This squeezing/releasing of the infusion tube, while the inlet valve and the outlet valve remain closed, may be repeated, thereby allowing detection of a delayed/prolonged closing of the valves or air in the line.

Additionally, a method is provided including squeezing the section of the infusion fluid line confined by the closed inlet and outlet valves, and measuring the pressure or pressure change resulting from the squeezing, using a pressure sensor positioned between the inlet and outlet valves, in an air detection phase (also referred to herein as a "quality control phase"), performed between the intake phase and the delivery phase of the infusion pump cycle, when both the inlet and the outlet valves are closed (also referred to herein as a "safety zone"). The pressure measured over successive air detection phases of successive infusion pump cycles may be used to calculate the accumulated air in the infusion line that is delivered during the delivery phase to the subject. Typically, the controller determines, based on a predefined threshold value, whether to continue the delivery of infusion fluid to the subject or whether to stop the infusion, e.g., in the case of the accumulated air in the infusion line passing the predetermined threshold value.

Thus, the herein disclosed method and device enables measuring the pressure within a confined section of the infusion fluid line (a) prior to the initiation of a delivery session of fluid to a subject as part of a valve operation check, and (b) during an infusion pump cycle as part of an air detection phase, that occurs between the intake phase and the delivery phase of the infusion pump cycle, when both the inlet and the outlet valves are closed. The amount of air content in the single delivery cycle may be determined based on the pressure measurement, thus ensuring that an undesired amount of air is not delivered to a patient during infusion fluid delivery.

The valve operation check prior to a delivery session and the in-cycle air detection both utilize the same components of the infusion pump, i.e., the inlet valve, the outlet valve, the squeezing element, e.g., plunger, and a pressure sensor located between the inlet and outlet valves. Additionally, the valve operation check and the in-cycle air detection both include the same steps, i.e., closing the inlet valve and outlet valve in order confine a section of the fluid line, squeezing the confined section of the fluid line, measuring the pressure within the fluid in response to the squeezing, and subsequently relieving the pressure.

In addition, the herein disclosed method and device advantageously enables detecting prolonged/slow closing of the inlet valve and/or outlet valve.

Moreover, the herein disclosed method and device enables distinguishing between incomplete valve sealing of the tube and presence of air in the infusion fluid line.

As a further advantage, the herein disclosed method and device enables performing the in-cycle pressure measurement of air with the same component that detects occlusions.

There is therefore provided, in accordance with some applications of the present invention, a method for use with an infusion pump that comprises an inlet valve, an outlet valve, and a squeezing element, the squeezing element located between the inlet valve and the outlet valve and configured to squeeze a fluid line coupled to the infusion pump, the method including:

performing at least one round of valve operation check prior to initiation of a delivery session of fluid to a subject; and subsequently, after an intake phase and before a delivery phase of at least one infusion pump cycle, determining for the at least one infusion pump cycle an absolute amount of air in the fluid line, the at least one round of valve operation check and the determining of the amount of air in the fluid line each including the steps of:

(A) triggering closing the inlet valve to confine a section of the fluid line between the inlet valve and the outlet valve;

(B) squeezing, utilizing the squeezing element, the confined section of the fluid line;

(C) measuring the pressure within the confined section of the fluid line; and (D) subsequently, relieving the pressure in the confined section of the fluid line.

For some applications, measuring the pressure in the confined section of the fluid line includes measuring the pressure using at least one sensor selected from the group consisting of: a piezoelectric sensor, a gauge pressure sensor, an optical sensor, and a proximity sensor.

For some applications, squeezing the confined section of the fluid line includes moving the squeezing element from a Release position of the squeezing element toward a Squeeze position of the squeezing element, and measuring the pressure includes measuring the pressure while the squeezing element is positioned at a position that is between the Squeeze position of the squeezing element and the Release position of the squeezing element.

For some applications, relieving the pressure in the confined section of the fluid line includes raising the squeezing element, while the inlet valve and the outlet valve remain closed.

For some applications, relieving the pressure in the confined section of the fluid line includes raising the outlet valve, while (a) the squeezing element remains in the position that is between the Squeeze position of the squeezing element and the Release position of the squeezing element, and (b) the inlet valve remains closed.

For some applications, relieving the pressure in the confined section of the fluid line includes directly entering into the delivery stage of the delivery cycle, by raising the outlet valve simultaneously with lowering the squeezing element, while the inlet valve remains closed.

For some applications, the measured pressure is indicative of a relative air content in the fluid delivered during the at least one infusion pump cycle, and determining the absolute amount of air includes calculating a volume of air, based on (a) the delivered volume of fluid during the at least one infusion pump cycle and (b) the relative air content in the fluid delivered during the at least one infusion pump cycle.

For some applications, the squeezing and the measuring of the pressure are repetitively performed after the respective intake phase and before the respective delivery phase of each of a respective number of successive infusion pump cycles.

For some applications, the method further includes determining an accumulated amount of air based on the absolute amount of air determined for each of the respective infusion pump cycles.

For some applications, the method further includes entering the delivery phase by raising the outlet valve only when the accumulated amount of air in the fluid line is below a predetermined threshold value.

For some applications, the method further includes providing a signal in response to the accumulated amount of air in the fluid line being above a predetermined threshold value.

For some applications, the method further includes, in response to the at least one round of valve operation check, determining valve dysfunction of at least one valve selected from the group consisting of: the inlet valve and the outlet valve, valve dysfunction including delayed closing of the selected valve, delayed opening of the selected valve, or the selected valve being stuck in either an open or closed position.

For some applications, the method further includes providing a signal indicative of the valve dysfunction.

For some applications, the method further includes determining valve dysfunction in response to the pressure measured during the at least one round of valve operation check being below a predetermined threshold value.

There is further provided, in accordance with some applications of the present invention, an infusion pump including:
  an inlet valve;
  an outlet valve;
  a squeezing element located between the inlet valve and the outlet valve and configured to squeeze a fluid line coupled to the infusion pump;
  a pressure sensor; and
  electric circuitry configured to:
  (i) perform at least one round of valve operation check prior to initiation of a delivery session of fluid to a subject, and
  (ii) subsequently, after an intake phase and before a delivery phase of at least one infusion pump cycle, determine, for the at least one infusion pump cycle, an absolute amount of air in the fluid line,
  the at least one round of valve operation check and the determining of the amount of air in the fluid line each including the electric circuitry performing the steps of:
  (A) triggering closing the inlet valve to confine a section of the fluid line between the inlet valve and the outlet valve;
  (B) triggering squeezing, utilizing the squeezing element, of the confined section of the fluid line;
  (C) measuring the pressure within the confined section of the fluid line; and
  (D) subsequently, triggering relieving of the pressure in the confined section of the fluid line.

For some applications, the electric circuitry is configured to trigger the squeezing of the confined section of the fluid line by moving the squeezing element from a Release position of the squeezing element toward a Squeeze position of the squeezing element, and the electric circuitry is configured to measure the pressure by measuring the pressure while the squeezing element is positioned at a position that is between the Squeeze position of the squeezing element and the Release position of the squeezing element.

For some applications, the electric circuitry is configured to trigger the relieving of the pressure in the confined section of the fluid line by raising the squeezing element, while the inlet valve and the outlet valve remain closed.

For some applications, the electric circuitry is configured to trigger the relieving of the pressure in the confined section of the fluid line by raising the outlet valve, while (a) the squeezing element remains in the position that is between the Squeeze position of the squeezing element and the Release position of the squeezing element, and (b) the inlet valve remains closed.

For some applications, the electric circuitry is configured to trigger the relieving of the pressure in the confined section of the fluid line by directly entering into the delivery stage of the delivery cycle, by raising the outlet valve simultaneously with lowering the squeezing element, while the inlet valve remains closed.

For some applications, the measured pressure is indicative of a relative air content in the fluid delivered during the at least one infusion pump cycle, and the electric circuitry is configured to determine the absolute amount of air by calculating a volume of air, based on (a) the delivered volume of fluid during the at least one infusion pump cycle and (b) the relative air content in the fluid delivered during the at least one infusion pump cycle.

For some applications, the electric circuitry is configured to repetitively trigger the squeezing and measure the pressure after the respective intake phase and before the respective delivery phase of each of a respective number of successive infusion pump cycles.

For some applications, the electric circuitry is further configured to determine an accumulated amount of air based on the absolute amount of air determined for each of the respective infusion pump cycles.

For some applications, the electric circuitry is further configured to enter the delivery phase by raising the outlet valve only when the accumulated amount of air in the fluid line is below a predetermined threshold value.

For some applications, the electric circuitry is further configured to provide a signal in response to the accumulated amount of air in the fluid line being above a predetermined threshold value.

For some applications, the electric circuitry is further configured to, in response to the at least one round of valve operation check, determine valve dysfunction of at least one valve selected from the group consisting of: the inlet valve and the outlet valve, valve dysfunction including delayed closing of the selected valve, delayed opening of the selected valve, or the selected valve being stuck in either an open or closed position.

For some applications, the electric circuitry is further configured to provide a signal indicative of the valve dysfunction.

For some applications, the electric circuitry is further configured to determine valve dysfunction in response to the pressure measured during the at least one round of valve operation check being below a predetermined threshold value.

For some applications, the pressure sensor includes at least one sensor selected from the group consisting of: a piezoelectric sensor, a gauge pressure sensor, an optical sensor, and a proximity sensor.

There is further provided, in accordance with some applications of the present invention, a method for in-cycle pressure measurement in an infusion fluid line, the method including:

utilizing an infusion pump comprising an inlet valve, an outlet valve and a squeezing element, the squeezing element located between the inlet valve and the outlet valve;

triggering closing the inlet valve to confine a section of the fluid line between the inlet valve and the outlet valve;

squeezing, utilizing the squeezing element, the confined section of the fluid line;

measuring the pressure within the confined section of the fluid line;

relieving the pressure in the confined section of the fluid line;

the squeezing and the measuring of the pressure being performed after an intake phase and before a delivery phase of a single infusion pump cycle.

For some applications, relieving the pressure in the confined section of the fluid line includes raising the squeezing element, while the inlet valve and the outlet valve remain closed.

For some applications, relieving the pressure in the confined section of the fluid line includes raising the outlet valve, while the inlet valve remains closed and the squeezing element remains in its position.

For some applications, squeezing the confined section of the fluid line includes moving the squeezing element from a Release position of the squeezing element toward a Squeeze position of the squeezing element, and measuring the pressure includes measuring the pressure while the squeezing element is positioned at a position that is between the Squeeze position of the squeezing element and the Release position of the squeezing element.

For some applications, relieving the pressure in the confined section of the fluid line includes both raising the outlet valve and lowering the squeezing element, while the inlet valve remains closed.

For some applications, relieving the pressure in the confined section of the fluid line includes raising the outlet valve, while (a) the squeezing element remains in the position that is between the Squeeze position of the squeezing element and the Release position of the squeezing element, and (b) the inlet valve remains closed.

For some applications, relieving the pressure in the confined section of the fluid line includes directly entering into the delivery stage of the delivery cycle, by raising the outlet valve simultaneously with lowering the squeezing element, while the inlet valve remains closed.

For some applications, the method further includes determining, for the single infusion pump cycle, an absolute amount of air in the fluid line, based on the measured pressure.

For some applications, the measured pressure is indicative of a relative air content in the fluid delivered during the single infusion pump cycle, and determining the absolute amount of air includes calculating a volume of air, based on the delivered volume of fluid during the single infusion pump cycle.

For some applications, the squeezing and the measuring of the pressure are repetitively performed after the respective intake phase and before the respective delivery phase of each of a predetermined respective number of successive infusion pump cycles.

For some applications, the method further includes determining an accumulated amount of air based on the absolute amount of air determined for each of the respective infusion pump cycles.

For some applications, the method further includes entering the delivery phase by raising the outlet valve only when the accumulated amount of air in the fluid line is below a predetermined threshold value.

For some applications, the method further includes providing a signal in response to the accumulated amount of air in the fluid line being above a predetermined threshold value.

For some applications, the squeezing element is a plunger, and squeezing the confined section of the fluid line includes lowering the plunger.

For some applications, the method further includes analyzing the pressure measurement with respect to a value selected from the group consisting of: one or more previous pressure measurements and a predetermined pressure threshold value.

For some applications, the method further includes performing at least one round of valve operation check, each of the at least one round of valve operation check including squeezing the confined section of the fluid line, measuring the pressure in the confined section in response to the squeezing, and relieving the pressure in the confined section prior to initiating a delivery session.

For some applications, the method further includes determining valve dysfunction of at least one valve selected from the group consisting of: the inlet valve and the outlet valve, valve dysfunction including delayed closing of the selected valve, delayed opening of the selected valve, or the selected valve being stuck in either an open or closed position.

For some applications, the method further includes providing a signal indicative of the valve dysfunction.

For some applications, the method further includes determining valve dysfunction in response to the pressure measured during the at least one round of valve operation check being below a predetermined threshold value.

For some applications, measuring the pressure in the confined section of the fluid line includes measuring the pressure using at least one sensor selected from the group consisting of: a piezoelectric sensor, a gauge pressure sensor, an optical sensor, and a proximity sensor.

There is further provided, in accordance with some applications of the present invention, an infusion pump including:
an inlet valve;
an outlet valve;
a squeezing element located between the inlet valve and the outlet valve;
a force sensor; and
electric circuitry configured to perform an in-cycle pressure measurement by:
triggering closing of the inlet valve to confine a section of a fluid line between the inlet valve and the outlet valve;
triggering the squeezing element to squeeze the confined section of the fluid line;
measuring the pressure in the confined section of the fluid line in response to the squeezing, by receiving a signal from the force sensor; and
triggering relieving of the pressure in the confined section of the fluid line;
the squeezing and the measuring of the pressure being performed after an intake phase and before a delivery phase of a single infusion pump cycle.

For some applications, the electric circuitry is configured to trigger the relieving of the pressure in the confined section of the fluid line by raising the squeezing element, while the inlet valve and the outlet valve remain closed.

For some applications, the electric circuitry is configured to trigger the squeezing of the confined section of the fluid line by moving the squeezing element from a Release position of the squeezing element toward a Squeeze position of the squeezing element, and the electric circuitry is configured to measure the pressure while the squeezing element is positioned at a position that is between the Squeeze position of the squeezing element and the Release position of the squeezing element.

For some applications, the electric circuitry is configured to trigger the relieving of the pressure in the confined section of the fluid line by both raising the outlet valve and lowering the squeezing element, while the inlet valve remains closed.

For some applications, the electric circuitry is configured to trigger the relieving of the pressure in the confined section of the fluid line by raising the outlet valve, while (a) the squeezing element remains in the position that is between the Squeeze position of the squeezing element and the Release position of the squeezing element, and (b) the inlet valve remains closed.

For some applications, the electric circuitry is configured to trigger the relieving of the pressure in the confined section of the fluid line by directly entering into the delivery stage of the delivery cycle, by raising the outlet valve simultaneously with lowering the squeezing element, while the inlet valve remains closed.

For some applications, the electric circuitry is further configured to determine, for the single infusion pump cycle, an absolute amount of air in the confined section of the fluid line, based on the measured pressure.

For some applications, the measured pressure is indicative of a relative air content in the fluid delivered during the single infusion pump cycle, and the electric circuitry is configured to determine the absolute amount of air by calculating a volume of air, based on the delivered volume of fluid during the single infusion pump cycle.

For some applications, the electric circuitry is configured to repetitively trigger the squeezing and the measuring of the pressure after the respective intake phase and before the respective delivery phase of each of a predetermined respective number of successive infusion pump cycles.

For some applications, the electric circuitry is further configured to determine an accumulated amount of air based on the absolute amount of air determined for each of the respective infusion pump cycles.

For some applications, the electric circuitry is further configured to trigger entering the delivery phase, by raising the outlet valve only when the accumulated amount of air in the fluid line is below a predetermined threshold value.

For some applications, the electric circuitry is configured to provide a signal in response to the accumulated amount of air in the fluid line being above a predetermined threshold value.

For some applications, the squeezing element is a plunger, and the electric circuitry is configured to trigger the squeezing element to squeeze the confined section of the fluid line by lowering the plunger.

For some applications, the electric circuitry is further configured to perform at least one round of valve operation check, each of the at least one round of valve operation check including squeezing the confined section of the fluid line, measuring the pressure in the confined section in response to the squeezing, and relieving the pressure in the confined section prior to initiating a delivery session.

For some applications, the electric circuitry is configured to determine valve dysfunction of at least one valve selected from the group consisting of: the inlet valve and the outlet valve, valve dysfunction including delayed closing of the selected valve, delayed opening of the selected valve, or the selected valve being stuck in either an open or closed position.

For some applications, the electric circuitry is configured to determine valve dysfunction in response to the pressure measured during the at least one round of valve operation check being below a predetermined threshold value.

For some applications, the electric circuitry is configured to perform at least two rounds of valve operation check.

For some applications, the force sensor includes at least one sensor selected from the group consisting of: a piezoelectric sensor, a gauge pressure sensor, an optical sensor, and a proximity sensor.

There is further provided, in accordance with some applications of the present invention, an infusion pump configured for measuring pressure in an infusion fluid line, the infusion pump including:
an inlet valve;
an outlet valve;
a squeezing element located between the inlet valve and the outlet valve;
a force sensor; and
electric circuitry configured to perform at least one round of valve operation check, the valve operation check including:
triggering closing of the inlet valve to confine a section of the fluid line between the inlet valve and the outlet valve,
triggering the squeezing element to squeeze the confined section of the fluid line,
detecting pressure in the confined section of the fluid line in response to the squeezing, by receiving a signal from the force sensor; and
triggering relieving of the pressure in the confined section of the fluid line;
the at least one round of valve operation check being performed prior to initiation of a delivery session.

For some applications, the electric circuitry is configured to determine valve dysfunction of at least one valve selected from the group consisting of: the inlet valve and the outlet valve, valve dysfunction including delayed closing of the selected valve, delayed opening of the selected valve, or the selected valve being stuck in either an open or closed position.

For some applications, the electric circuitry is configured to distinguish between (a) delayed closing of the valve, and (b) the valve being stuck in either an open or closed position.

For some applications, the electric circuitry is configured to determine valve dysfunction in response to the pressure measured during the at least one round of valve operation check being below a predetermined threshold value.

For some applications, the electric circuitry is further configured to provide a signal indicative of the valve dysfunction.

For some applications, the electric circuitry is configured to perform at least two rounds of valve operation check.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

FIG. 4A schematically depicts the inlet valve position, outlet valve position, and squeezing element position during different stages of an exemplary infusion pump cycle, in which the pressure generated during an air detection procedure is released by raising the squeezing element, in accordance with some applications of the present invention;

DETAILED DESCRIPTION OF THE INVENTION

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

As used herein, the term "in cycle measurement" refers to a method performed during a single infusion pump cycle within a session of infusion fluid delivery. As used herein, the terms "infusion pump cycle" and "single infusion pump cycle" refer to a cycle including a single "intake phase", during which infusion fluid is taken in from an infusion fluid reservoir, a single "delivery phase", during which the infusion fluid taken in during the intake phase is delivered to the patient, and "safety zones", during which the inlet valve and the outlet valve remain closed.

According to some embodiments, the "total delivery", also referred to herein as a "delivery session", i.e., the total prescribed dose of infusion fluid delivered to a patient, may include one or more infusion pump cycles. According to some embodiments, the "total delivery" may include a plurality of infusion pump cycles. As used herein, the term "plurality", with regards to infusion pump cycles, may include more than 10, more than 20, more than 50 or more than 100 infusion pump cycles. Each possibility is a separate embodiment.

Figure 1:
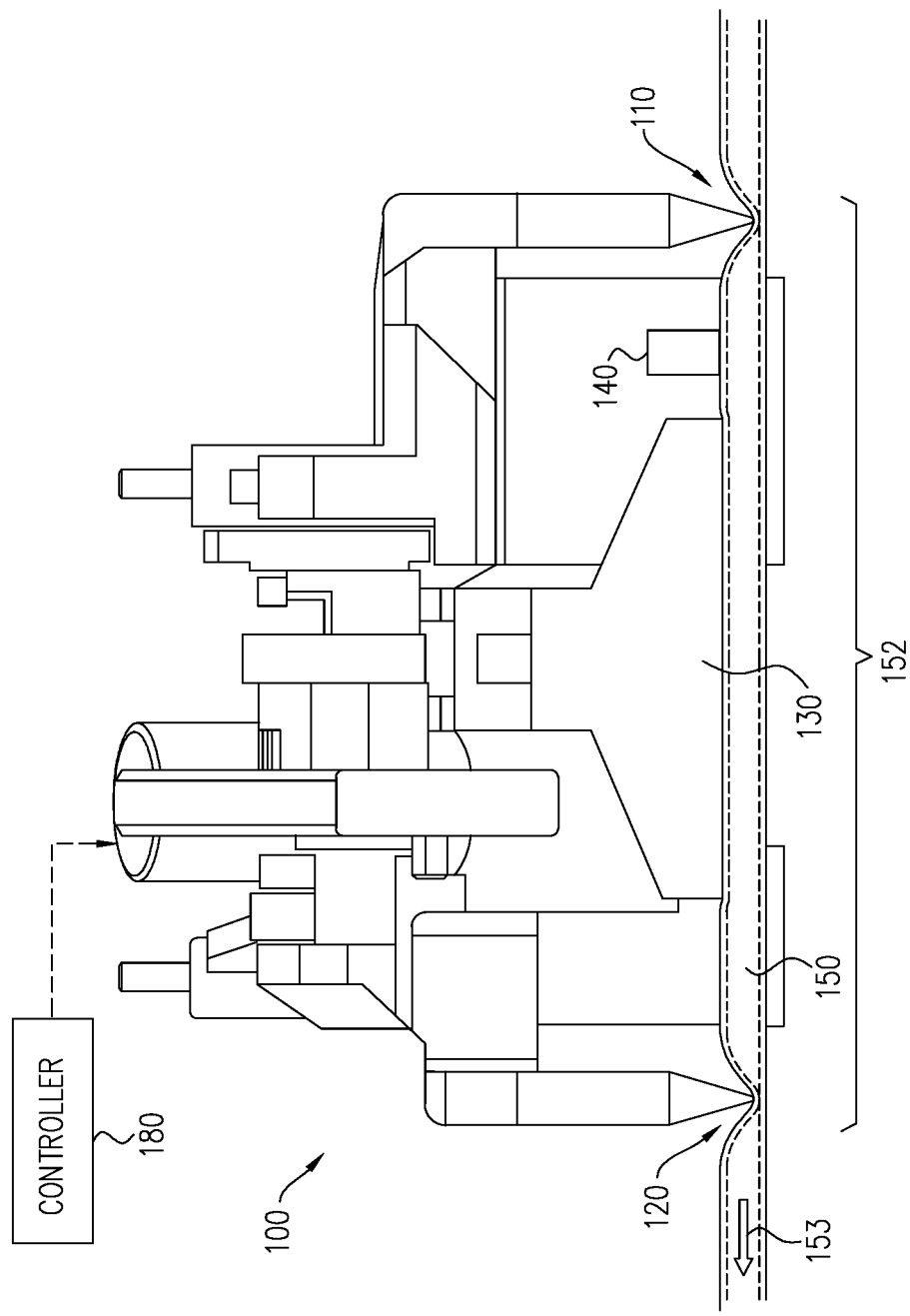
FIG. 1 schematically illustrates an infusion pump mechanism during an air detection procedure, in accordance with some applications of the present invention.

Reference is now made to FIG. 1, which schematically illustrates an infusion pump 100 during an air detection procedure, in accordance with some applications of the present invention. Infusion pump 100 includes an inlet valve 110 configured to regulate the flow from an infusion fluid reservoir (not shown), such as an infusion bag, into an infusion fluid line 150, an outlet valve 120 configured to regulate flow from infusion fluid line 150 to a patient (not shown), and a controller 180 configured to control the operation of infusion pump 100. Infusion pump 100 further includes a squeezing element 130 configured to squeeze infusion fluid line 150, thereby causing infusion fluid flow to the patient when outlet valve 120 is open. For some applications, squeezing element 130 may be an infusion pump plunger, and squeezing the infusion line may be achieved by lowering the plunger.

During the intake phase of an infusion pump cycle, inlet valve 110 is opened, while outlet valve 120 is kept closed and squeezing element 130 is raised to an upper position (further described hereinbelow as a "Release position") allowing infusion fluid to flow downstream of inlet valve 110. Upon completion of the intake phase, inlet valve 110 is closed, thus closing off infusion fluid line 150 by both inlet valve 110 and outlet valve 120, thereby forming a confined section 152 of fluid line 150. The phase of pump 100 during which both inlet valve 110 and outlet valve 120 are closed is also referred to hereinbelow as a "safety zone." During the safety zone, after the intake phase and before the delivery phase, an air detection phase, also referred to herein as a "quality control phase," may be carried out. Subsequently, the delivery phase of the infusion pump cycle may be initiated by opening outlet valve 120 and lowering squeezing element 130, thereby squeezing infusion line 150. Arrow 153 represents the direction of fluid flow within fluid line 150 during the delivery phase.

During the air detection phase, confined fluid line section 152 (confined by inlet valve 110 and outlet valve 120), is squeezed by squeezing element 130, thereby elevating the pressure within confined section 152. The pressure within confined section 152 is measured in response to the squeezing using a pressure sensor 140 and may be used to determine how much air is in confined section 152 of fluid line 150, as further described hereinbelow.

The pressure measured over successive air detection phases of successive infusion pump cycles, i.e., after the respective intake phase and before the respective delivery phase of each of a respective number of successive infusion pump cycles, may be used to calculate the accumulated air in infusion line 150, as further described hereinbelow with reference to FIG. 2. Typically, pump 100 enters the delivery phase of a pump cycle by raising outlet valve 110 only when the accumulated amount of air in fluid line 150 is below a predetermined threshold. For some applications, controller 180 provides a signal in response to the accumulated amount of air in fluid line 150 being above the predetermined threshold.

According to some embodiments, pressure sensor 140 may be a piezoelectric sensor, a gauge pressure sensor, an optical sensor, a proximity sensor or any other suitable sensor or combination of sensors configured to measure pressure and/or parameters indicative of the pressure in confined section 152 of infusion line 150. Typically, pressure sensor 140 is positioned between inlet valve 110 and outlet valve 120.

For some applications, the squeezing of confined section 152 of infusion tube 150 is performed in a position where squeezing element 130 partially squeezes tube 150, thereby inducing a pressure rise to a determined pressure threshold (as further described hereinbelow). For some applications, the descending of squeezing element 130, i.e., lowering squeezing element 130, may increase the pressure within confined section 152 by up to 2 bar. For some applications, the subsequent ascending of squeezing element 130, caused by raising squeezing element 130, can create up to 0.5 bar of vacuum.

For some applications, as further described hereinbelow with reference to FIG. 4A, upon completion of the air detection phase the pressure in confined section 152 of fluid line 150 is relieved prior to opening of outlet valve 120 in order to avoid a bolus of infusion fluid being delivered to the patient upon opening of outlet valve 120. Alternatively, for some applications, the pressure in confined section 152 of fluid 150 is relieved by opening of outlet valve 120 at the beginning of the delivery phase and the resulting bolus is accounted for as part of the delivery volume of infusion fluid for the pump cycle, as further described hereinbelow with reference to FIG. 4B.

FIG. 1 also depicts infusion pump 100 during a round of valve operation checking (hereinbelow, "valve operation check") prior to the initiation of a delivery session of infusion fluid to the subject, as further described hereinbelow. Typically, both the round of valve operation check and the determining of the amount of air in fluid line 150 each include the steps of:

(A) triggering closing inlet valve 110 to confine section 152 of fluid line 150 between inlet valve 110 and outlet valve 120;

(B) utilizing squeezing element 130 to squeeze confined section 152 of fluid line 150;

(C) measuring the pressure within confined section 152 of fluid line 150; and (D) subsequently, relieving the pressure in confined section 152 of fluid line 150.

Figure 2:
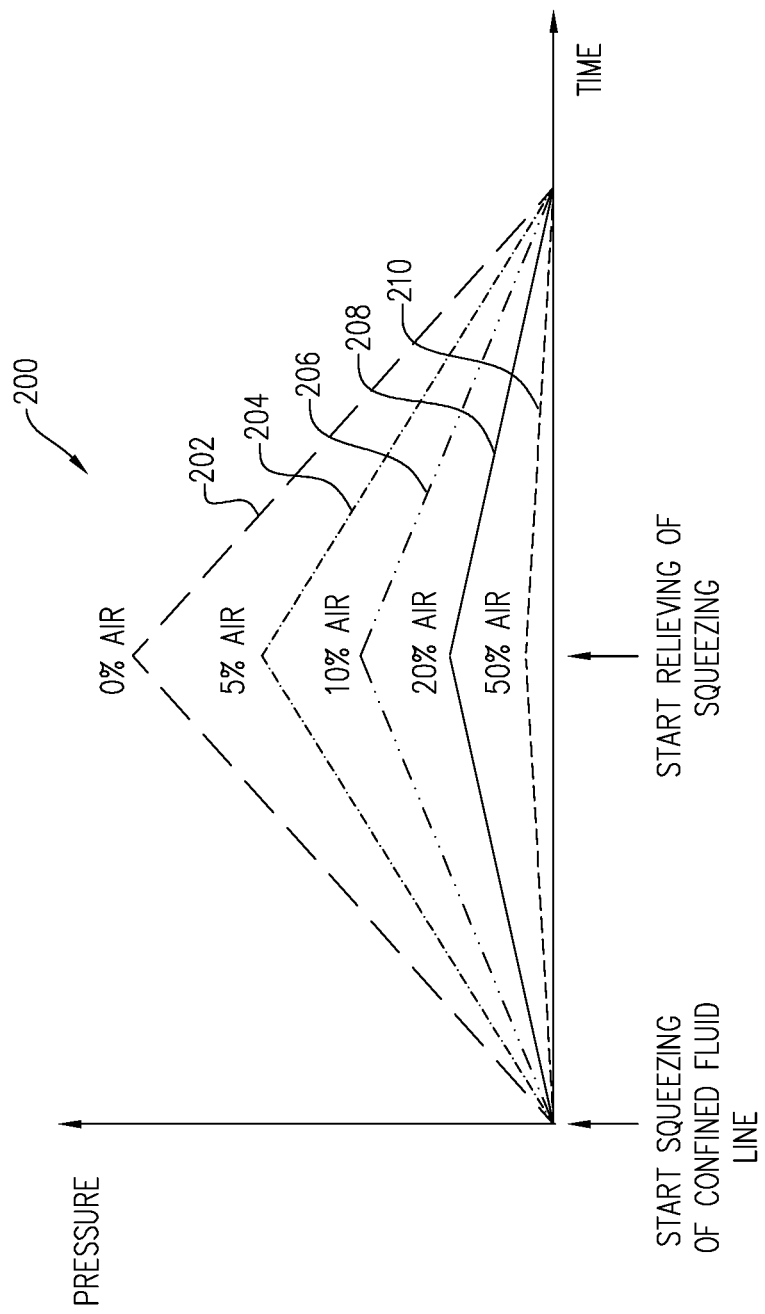
FIG. 2 shows an illustrative graph of pressure values obtained when squeezing a confined section of a fluid line containing various percentages of air, in accordance with some applications of the present invention.

Reference is now made to FIG. 2, which shows a graph 200 depicting, for respective amounts of air within confined section 152, illustrative pressure measurement values within confined section 152 of infusion fluid line 150 in response to squeezing confined section 152 and subsequently releasing confined section 152, using infusion pump 100, in accordance with some applications of the present invention.

As seen from graph 200, when a confined section of an infusion fluid line (for example an infusion fluid line confined by an infusion pump's inlet and outlet valves being closed, e.g., confined section 152 of infusion line 150, confined by closed inlet valve 110 and outlet valve 120 of pump 100) is squeezed (for example by lowering squeezing element 130), the pressure in the confined section increases, and this pressure change can be detected using a pressure sensor (e.g., pressure sensor 140). As further seen, the extent of the increase in pressure due to squeezing the confined section depends on the amount of air that is present in the infusion fluid line. For example, when infusion line 150 is devoid of air, the pressure increases to a maximum value when squeezing element 130 is used to squeeze confined section 152. This is depicted by curve 202 of graph 200, which depicts the highest increase in pressure due to squeezing confined section 152 when confined section 152 contains 0% air. However, when air is present within confined section 152, due to the compressibility of air, the pressure increase in response to squeezing confined section 152 is reduced as a function of the amount of air present. The pressure value measured in confined section 152 of infusion fluid line 150 is indicative of a relative amount of air in infusion fluid line 150 during a particular infusion pump cycle. This is depicted by curves 204, 206, 208, and 210 of graph 200, which show successively smaller pressure increases in response to squeezing confined section 152 when fluid line 150 contains, respectively, 5% air, 10% air, 20% air, and 50% air. Based on the measured pressure, an absolute amount of air in infusion line 150 may be determined, e.g., calculated, based on the volume of delivered fluid during one infusion pump cycle (e.g., typical volumes of delivered fluid in a single pump cycle are 10 microliters-500 microliters).

For some applications, the pressure measured over successive air detection phases of successive infusion pump cycles, i.e., after the respective intake phase and before the respective delivery phase of each of a respective number of successive infusion pump cycles, may be used to calculate the accumulated air in infusion line 150. An accumulated absolute amount of air determined over successive infusion pump cycles, as described above, may serve as an indication of whether delivery of an infusion fluid to a patient can be carried out safely. For example, if the accumulated amount of air reaches a threshold value (e.g., at least 200 microliters, e.g., at least 500 microliters, e.g., at least 1 ml, e.g., at least 1.5 ml), the delivery session may be terminated/halted and optionally a signal is generated by controller 180, e.g., an alert or alarm is triggered. If the accumulated amount of air is below the threshold value, the delivery session is continued.

For some applications, successive air detection phases of successive infusion pump cycles refers to pressure measurements obtained during a time window of at least 10 minutes of pump operation e.g., 15 minutes, e.g., 20 minutes of pump operation. If during the specified time window of pump operation the accumulated amount of air does not reach the threshold value, then the delivery session of the infusion fluid to the subject continues and the accumulated air over the next specified time window. Typically, a moving time window is used with the beginning of the time window (i.e., the beginning of the time window of at least 10 minutes, e.g., 15 minutes, e.g., 20 minutes) moving in increments of 30 seconds, 1 minute, or 2 minutes. Thus, after each incremental movement of the time window the accumulated air is calculated for the immediately preceding at least 10 minutes e.g., 15 minutes, e.g., 20 minutes of pump operation. Thus, pump 100 continuously measures the accumulated air in the last 10, 15 or 20 minute window of pump operation.

For some applications, the accumulated amount of air is determined as the total amount of air obtained during a defined number of successive cycles, wherein the defined number of cycles (e.g., at least 2 and/or less than 50 infusion pump cycles) depends on single cycle delivery volume. If the accumulated amount of air reaches the threshold value (e.g., at least 200 microliters, e.g., at least 500 microliters, e.g., at least 1 ml, e.g., at least 1.5 ml) the delivery session is terminated/halted and optionally a signal is generated by controller 180, e.g., an alert or alarm is triggered. If the accumulated amount of air after the defined number of successive cycles is below the threshold value, the delivery session is continued and the accumulated air over the next number of successive cycles determined.

Figure 3:
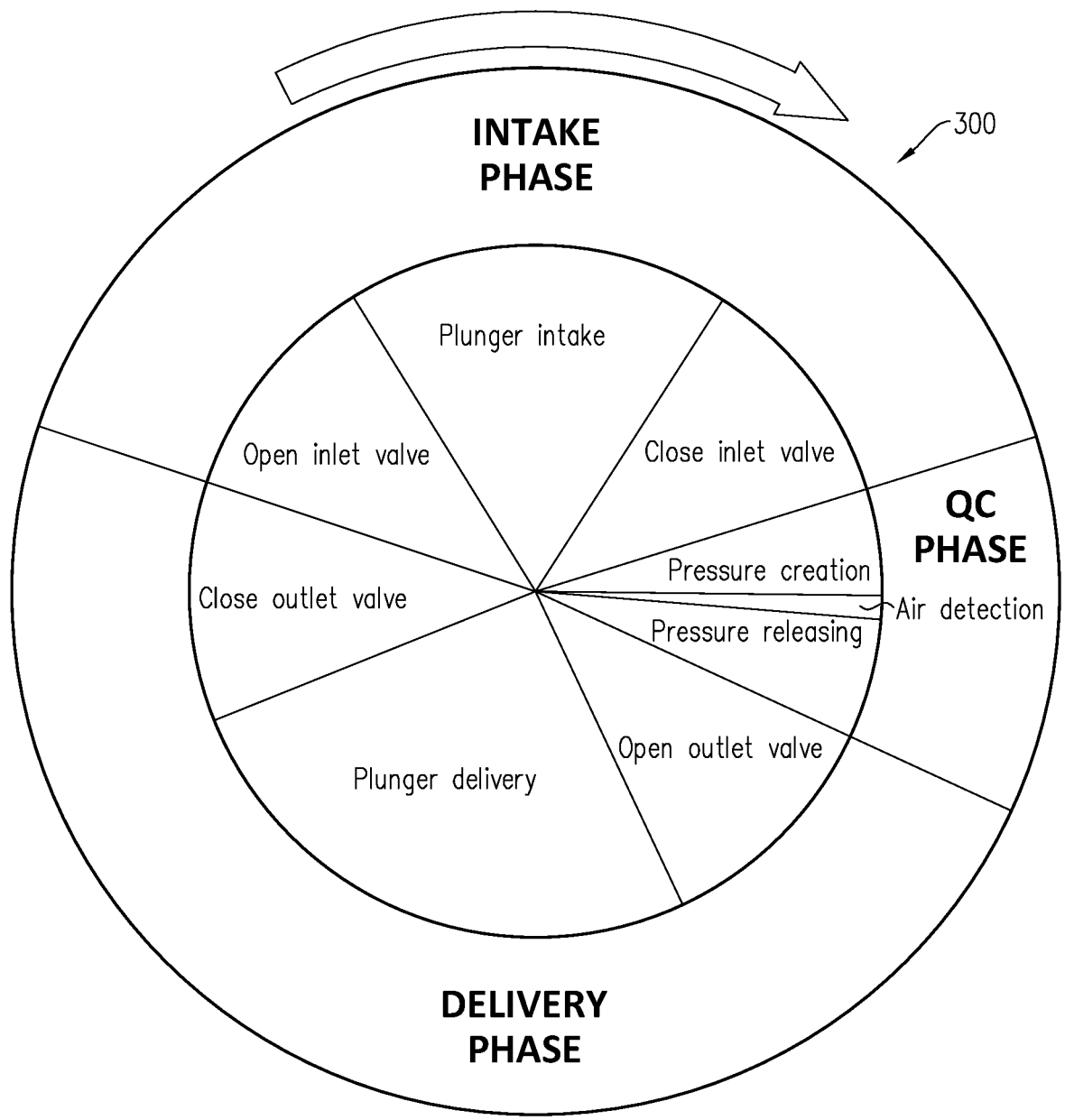
FIG. 3 is an illustrative pie chart of an infusion pump cycle, in accordance with some applications of the present invention.

Reference is now made to FIG. 3, which is an illustrative pie chart 300 of an infusion pump cycle of pump 100, in accordance with some applications of the present invention. The depicted infusion pump cycle includes, as is typical to most infusion pump cycles, an intake phase, during which an infusion fluid is taken in from a fluid reservoir, such as an infusion fluid bag, and a delivery phase during which the fluid is delivered to the patient. A total delivery session typically includes numerous such infusion pump cycles.

In addition, the depicted infusion pump cycle further includes a "QC" (quality control) phase, in a safety zone occurring between the intake phase and the delivery phase, during which pressure measurements and air detection are performed, as described hereinabove. During the quality control phase of the pump cycle, the infusion line squeezing starts from the upper squeezing element position (i.e., the position of squeezing element 130 at the end of the intake phase) to a partially squeezing state (further described hereinbelow with reference to FIG. 4A), while the pressure is measured. For some applications, the completion of this phase can include returning squeezing element 130 to its upper position while the valves are still closed. Alternatively, for some applications, the completion of this phase includes opening of the downstream valve while squeezing element 130 remains in the partially squeezed position.

As illustrated, the intake phase of the infusion pump cycle includes a first step of opening inlet valve 110 of infusion pump 100 (while outlet valve 120 is closed). Subsequently, plunger 130 is positioned in an upper position (e.g., by raising squeezing element 130), thereby creating a suction force and infusion fluid intake. Once a sufficient amount of infusion fluid has been taken into infusion line 150, inlet valve 110 is closed (while outlet valve 120 remains closed) and thus the intake phase completed.

During the subsequent QC phase, confined section 152 of infusion fluid line 150 (confined by the closed inlet valve 110 and outlet valve 120) is squeezed by squeezing element 130. Typically, confined section 152 of infusion line 150 is partially squeezed by an amount that is less than the squeezing of infusion line 150 during the delivery phase (e.g., 3% to 50%, or 50% to 100% of the squeezing during the delivery phase). The pressure change resulting from the squeezing of confined section 152 during the QC phase is measured by pressure sensor 140. As described hereinabove, the decision of whether pump 100 continues on to the delivery phase following the QC phase may be based on the detected pressure values over successive infusion pump cycles, which serve as an indication of accumulated air content within infusion line 150. Provided the accumulated amount of air is below a predetermined threshold, the outlet valve is opened for delivery and the infusion fluid line is squeezed, thereby bringing about delivery of the infusion fluid to the patient. Once the delivery has been completed, the outlet valve is closed, and the delivery phase completed. The subsequent infusion pump cycle may be halted if above-threshold values accumulated air are obtained, e.g., if an undesired amount of air is detected in infusion fluid line 150. Typically, upon completion of the QC phase, squeezing element 130 is raised, or outlet valve 120 is partially opened, in order to release the pressure inside confined section 152 of fluid line 150, so as to avoid bolus delivery to the patient.

It is understood that upon completion of the delivery phase, a subsequent intake phase (of a subsequent infusion pump cycle) may be commenced.

For some applications, the above-described air detection method may be performed during each of the infusion pump cycles, constituting the total delivery of the fluid to the subject. For some applications, the above-described method may be performed periodically, e.g., every two infusion pump cycles, every five infusion pump cycles, or every ten infusion pump cycles.

For some applications, the air detection phase may have a duration of less than five seconds, e.g., less than two seconds, e.g., less than one second.

Reference is now made to FIG. 4A, which is an illustrative table 400a that schematically depicts inlet valve 110 position, outlet valve 120 position, and squeezing element 130 position during different stages of an exemplary infusion pump cycle, wherein the pressure generated during an air detection procedure by squeezing confined section 152 of infusion line 150 with squeezing element 130 is released by moving squeezing element 130 back to its pre-squeezing position, in accordance with some applications of the present invention.

According to some embodiments, the releasing of the pressure in confined section 152 of infusion line 150 may be achieved by releasing squeezing element 130 from squeezing confined section 152, e.g., by raising squeezing element 130. As used throughout the present application, including in the claims, ascending of squeezing element 130, e.g., the plunger, is caused by raising squeezing element 130, and descending of squeezing element 130, e.g., the plunger, is caused by lowering squeezing element 130.

The pump cycle phases are schematically depicted in table 400a and occur sequentially from left to right. In the delivery phase, inlet valve 110 is closed (depicted by graph line 402a being at DOWN for the duration of the delivery phase). Outlet valve 120 is opened at the beginning of the delivery phase (depicted by graph line 404a going from DOWN to UP in the first column of the delivery phase) followed by a subsequent positioning of squeezing element 130 in the Squeeze position (depicted by graph line 406a going from Release to Squeeze in the second column of the delivery phase). Once delivery is completed, outlet valve 120 is closed (depicted by graph line 404a moving back to DOWN in the third column of the delivery phase).

Following the delivery phase, a security/safety zone occurs, during which inlet valve 110 is closed (graph line 402a remains at DOWN), outlet valve 120 is closed (graph line 404a remains at DOWN), and squeezing element 130 is maintained in squeezing position (graph line 406a remains at Squeeze). The safety zone may last about at least 10 ms and/or less than a couple of minutes, e.g., at least 10 ms and/or less than 1 min, e.g., at least 100 ms and/or less than 30 seconds, e.g., at least 100 ms and/or less than 10 seconds, e.g., at least 0.5 sec and/or less than 5 seconds, or any other suitable duration that is, for example, within the range of 10 ms to 2 min. This safety zone is usually called a break-before-make sequence to ensure proper closing of the valves prior to opening the other valve. This is done for every valve transition.

During the intake phase, outlet valve 120 remains closed (depicted by graph line 404a being at DOWN for the duration of the intake phase). Inlet valve 110 opens at the beginning of the intake phase (depicted by graph line 402a going from DOWN to UP in the first column of the intake phase) followed by a subsequent releasing of squeezing element 130 (depicted by graph line 406a going from Squeeze to Release in the second column of the delivery phase). Once the intake of the infusion fluid is completed, inlet valve 110 is closed (depicted by graph line 402a moving to DOWN in the third column of the intake phase). Subsequently, another safety zone occurs.

Following the completion of the intake phase, a Quality Control (QC) phase is commenced which begins with a safety zone during which inlet valve 110 and outlet valve 120 are closed and squeezing element 130 is maintained in the Release position (depicted by the safety zone column between the intake phase and the QC phase of table 400a). The safety zone typically lasts for less than 1 second, followed by the QC phase in which air detection is performed, as described hereinabove.

The QC/air detection phase includes maintaining section 152 of infusion fluid line 150 confined by inlet valve 110 and outlet valve 120, while partially squeezing confined section 152. Typically, partially squeezing confined section 152 is achieved by positioning squeezing element 130 in a position between the Squeeze and Release positions and measuring the pressure or the change in the pressure within confined section 152 as a result of the squeezing (depicted by graph line 406a moving from Release to a position between Release and Squeeze in the QC phase column of table 400a). As used throughout the present application, including in the claims, (a) the "Squeeze position" refers to the position of the squeezing element, e.g., plunger, after its maximal descent, e.g., upon completion of delivery of the fluid to the patient for a given cycle, and (b) the "Release position" refers to the position of the squeezing element, e.g., plunger, after its maximal ascent, e.g., upon the completion of intaking the fluid from the reservoir for a given cycle.

For some applications, the positioning of squeezing element 130 is determined based on the volume between the two valves and the limitation that when there is no air is within confined tube section 152, the pressure resulting from the partial squeezing of confined section 152 should not increase above 1.5 bar. Additionally, the partial squeezing of confined section 152 is intended to use less than complete plunger squeezing, while providing enough pressure such that if there is air in the fluid line, e.g., up to 50% air in the fluid line, enough pressure is generated to enable detection of and differentiating between valve dysfunction, e.g., where at least one of the valves is not closed when it should be, and air in the fluid line. Once the air detection is completed, squeezing element 130 is re-positioned in its Release position, so as to release the pressure within confined section 152 while inlet valve 110 and outlet valve 120 remain closed (depicted by graph line 406a returning to Release in the QC phase column of table 400a). A subsequent safety zone (with typically a duration of less than 1 second), during which inlet valve 110 and outlet valve 120 are closed and squeezing element 130 is maintained in the Release position, occurs prior to pump 100 returning to the delivery phase.

Figure 4B:
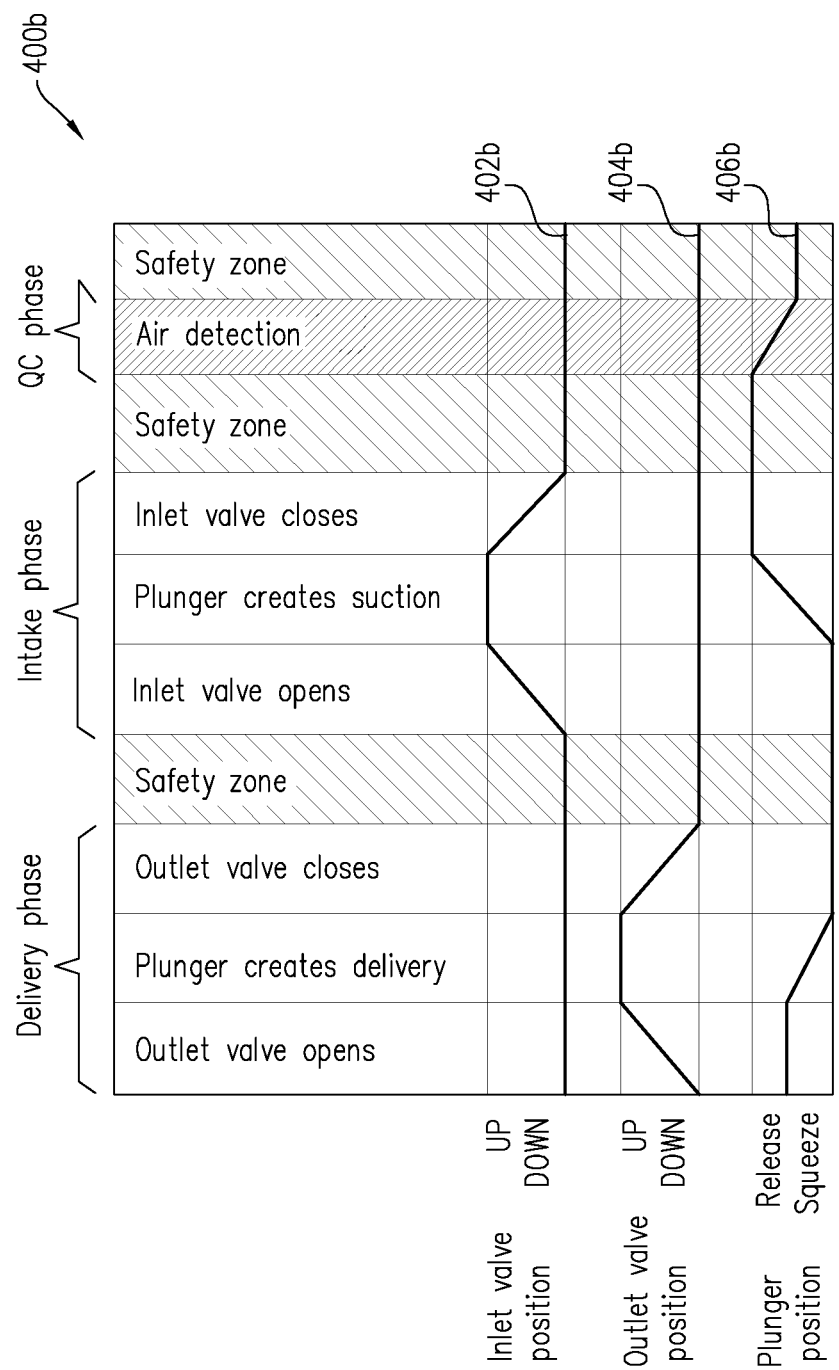
FIG. 4B schematically depicts the inlet valve position, outlet valve position, and squeezing element position during different stages of an exemplary infusion pump cycle, in which the pressure generated during an air detection procedure is released by opening of the outlet valve, in accordance with some applications of the present invention.

Reference is now made to FIG. 4B, which is an illustrative table 400b that schematically depicts inlet valve 110 position, outlet valve 120 position, and squeezing element 130 position during different stages of an exemplary infusion pump cycle, wherein the pressure generated during an air detection procedure by squeezing confined section 152 of infusion line 150 with squeezing element 130 is released into the downstream fluid line by opening of outlet valve 120, in accordance with some applications of the present invention. The pump cycle phases are schematically depicted in table 400b and occur sequentially from left to right.

For some applications, the releasing of the pressure in confined section 152 of infusion line 150 may be achieved by the ascending of the outlet valve 120, i.e., by raising outlet valve 120, while (a) squeezing element 130 is maintained in its previous position, i.e., partially squeezing infusion line 150 and (b) inlet valve 110 remains closed. For some applications, the releasing of the pressure in confined section 152 of infusion line 150 may be achieved by both the ascending of the outlet valve 120 and the descending of the squeezing element 130. According to some embodiments, the releasing of the pressure in confined section 152 of infusion line 150 may be achieved by direct entry into the delivery stage of the delivery cycle, by the ascending of the outlet valve 120 simultaneously with the descending of the squeezing element 130, while inlet valve 110 remains closed.

As used throughout the present application, including in the claims, ascending of inlet valve 110 or outlet valve 120 is caused by raising the respective valve, and descending of inlet valve 110 or outlet valve 120 is caused by lowering the respective valve.

It is noted that the intake phase depicted in table 400b is identical to that of table 400a.

Similarly to as described above with reference to FIG. 4A, following the completion of the intake phase, a Quality Control (QC) phase is commenced which begins with a safety zone, during which inlet valve 110 and outlet valve 120 are closed and squeezing element 130 is maintained in the Release position (depicted by the safety zone column between the intake phase and the QC phase of table 400b). The safety zone typically lasts for less than 1 second, followed by the QC phase in which air detection is performed, as described hereinabove.

The QC/air detection phase includes maintaining section 152 of infusion fluid line 150 confined by inlet valve 110 and outlet valve 120, while partially squeezing confined section 152. As described above, typically, partially squeezing confined section 152 is achieved by positioning squeezing element 130 in a position between the Squeeze and Release positions (based on the same rationale as described for FIG. 4A) and measuring the pressure or the change in the pressure within confined section 152 as a result of the squeezing (depicted by graph line 406b moving from Release to a position between Release and Squeeze in the QC phase column of table 400b). After the QC phase is competed, another safety zone occurs in which inlet valve 110 and outlet valve 120 remain closed and squeezing element 130 remains partially squeezing confined section 152.

For some applications, once the QC phase is completed, the pressure generated by the partial squeezing of confined section 152 of infusion fluid line 150 by squeezing element 130 is released at the beginning of the delivery phase by an initial partial opening of outlet valve 120 (to an upper position where 30%-98% of the area of the inner tube cross section immediately below outlet valve 120 is closed while squeezing element 130 is kept at its partially squeezing position, followed by continued opening of outlet valve 120 once the pressure is released (depicted by graph line 404b going from DOWN to UP in the first column of the delivery phase while graph line 406b remains at the position between Release and Squeeze). Thus, confined section 152 is partially opened and the pressure released towards the infusion fluid downstream line. Advantageously, this controlled partial opening of downstream valve 120 by a predetermined amount and at a predetermined rate allows pump 100 to control the bolus rate delivered to the downstream line as outlet valve 120 is opened. This bolus volume can thus be accounted for in the total delivered volume for the pump cycle. The delivery phase continues by continuing the opening of the outlet valve and then squeezing by squeezing element 130 (depicted by graph line 406b going from the position between Release and Squeeze to Squeeze in the second column of the delivery phase) in order to deliver the rest of the volume of fluid for the pump cycle. Once delivery is completed, outlet valve 120 is closed (depicted by graph line 404b moving back to DOWN in the third column of the delivery phase).

Figure 5:
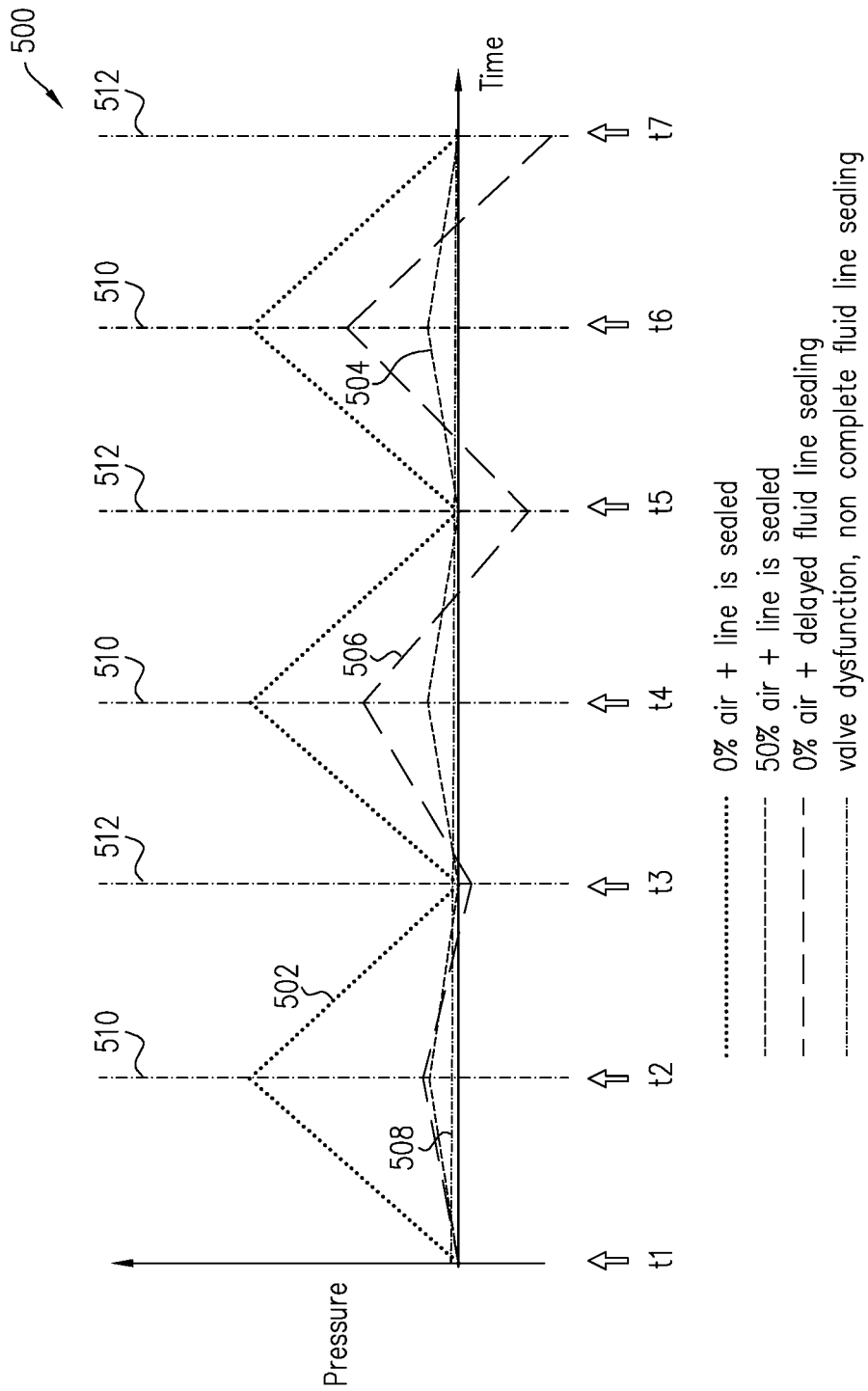
FIG. 5 is an illustrative graph of pressure values obtainable for repetitive pressure measurements made in a fluid line which is sealed and devoid of air (dotted line); in a fluid line which is sealed and contains 50% air (dashed line); in a fluid line which is devoid of air but has delayed valve sealing (long-dashed line); and in a fluid line with valve dysfunction/no sealing (dot-dashed line), in accordance with some applications of the present invention.

Reference is now made to FIG. 5, which is an illustrative graph 500 of pressure values for repetitive pressure measurements made in a fluid line which is sealed and devoid of air (dotted curve 502); in a fluid line which is sealed and contains 50% air (dashed curve 504); in a fluid line which is devoid of air, but has delayed valve sealing (long-dashed curve 506); and in a fluid line with valve dysfunction/no sealing (dot-dashed curve 508), in accordance with some applications of the present invention. For some applications, the repetitive air test depicted in graph 500 is only performed before the start of the delivery session of infusion fluid to the subject, after the priming of infusion line 150 (either by the pump or manually).

After priming of infusion line 150, the QC phase may include numerous repetitions of squeezing/releasing confined section 152 of infusion line 150, while inlet valve 110 and outlet valve 120 remain closed, during at least one round of valve operation check. Such repetitions may enable distinguishing between an insufficient pressure value obtained as a result of air being present in confined section 152 of infusion line 150 and an insufficient pressure value obtained due to delayed sealing of the infusion line, e.g., if either inlet valve 110 or outlet valve 120 is still closing when squeezing element 130 is lowered. That is, for some applications, if only one squeezing/releasing of confined section 152 is performed and only one pressure measurement taken, then if insufficient pressure is measured it may not be easily possible to distinguish if the low pressure reading is due to too much air being in confined section 152 or due to either one of the valves not being properly closed.

Dashed lines 510, occurring at times t2, t4, and t6 of graph 500 represent the partial squeezing of confined section 152, i.e., when squeezing element 130 is in its partially squeezing position. Dashed lines 512, occurring at times t3, t5, and t7, represent the release of the pressure within confined section 152, either by raising squeezing element 130 or raising outlet valve 120 as described hereinabove with reference to FIGS. 4A and 4B respectively. Graph 500 depicts three repetitive cycles of squeezing/releasing of confined section 152, which may be performed as part of a valve operation check prior to the initiation of a delivery session of infusion fluid to the subject.

As seen from graph 500, when confined section 152 is properly sealed and devoid of air (represented by dotted curve 502 of graph 500), squeezing confined section 152 of infusion line 150 causes an increase in the pressure within confined section 152, followed by a similar, e.g., the same, increase in pressure obtained during pressure measurements taken as a result of subsequent squeezing of confined section 152. This is depicted by dotted curve 502 of the graph reaching the same pressure valve at times t2, t4, and t6.

If air is present in confined section 152 of infusion line 150 (represented by dashed curve 504 of graph 500 depicting 50% air within confined section 152), the pressure in confined section 152 does not reach as high a pressure value obtained when air is not present. However, as before, if inlet valve 110 and outlet valve 120 are fully closed, the same pressure values are obtained over subsequent squeezing-measuring-releasing cycles.

An undesired situation may be determined when the pressure in the fluid line is above a predetermined threshold value corresponding to a total accumulated air content threshold value, e.g., 200 microliters, 500 microliters, 1 ml, or 1.5 ml.

Valve dysfunction such as (a) delayed closing of inlet valve 110 and/or outlet valve 120, (b) delayed opening of inlet valve 110 and/or outlet valve 120, or (c) inlet valve 110 and/or outlet valve 120 being stuck in an open position, is determined in response to the valve operation check. For some applications, controller 180 may generate a signal indicative of the valve dysfunction. For example, valve dysfunction may be determined in the absence of pressure build up, i.e., in response to the pressure measured during the valve operation check being below a predetermined threshold, when confined section 152 is squeezed by squeezing element 130 (represented by dot-dashed curve 508 of graph 500). For some applications, the absence of sufficient pressure buildup during the valve operation check prior to a delivery session may be indicative of air in fluid line 150, e.g., due to improper priming. In such a case, the method may further include providing a signal indicative of valve dysfunction/air in line and holdup/cessation/termination of delivery initiation. This is in contrast to the air detection phase occurring during delivery, i.e., during the pump cycles as described hereinabove, where pressure is monitored during several subsequent cycles and accumulated air content is accounted for, such that if pump 100 does not detect a sufficient pressure rise during one particular cycle, the delivery is not stopped until the accumulated air content reaches the threshold value.

The pressure value/increase for 0% air when the valves are performing properly is calibrated during pump production and is typically in the range of 0-2 bar depending on the squeezing element position (e.g., 0 bar for no squeezing, and up to 2 bar for a squeezing position of the squeezing element 130). The pressure threshold value is set accordingly.

For some applications, when utilizing a sufficiently sensitive sensor, different thresholds may be set for "100% air" and for "inlet and outlet valves both open". When both valves are opened, no pressure increase will occur, as opposed to when confined section 152 contains 100% air, which will bring about a slight pressure increase when confined section 152 is squeezed.

For some applications, controller 180 of pump 100 may identify a pattern in the respective pressures measured during the repetitive squeezing-measuring-releasing cycles. The pattern of the measured pressures may be analyzed with respect to one or more previously-measured pressure patterns or one or more predetermined pressure patterns. For some applications, if the closing of inlet valve 110 and/or outlet valve 120 is slow (represented by long dashed curve 506 of graph 500), and thus the sealing of confined section 152 of infusion fluid line 150 is delayed, an initial pressure measurement in response to the first squeezing at time t2 may be low (and similar to that obtained when air is present in the infusion line). However, as the valve continues to close (or is delayed in closing), the pressure values gradually increase during measurements taken in response to subsequent squeezing/measuring/releasing cycles, e.g., at time times t4 and t6. Thus, for some applications, delayed closing of inlet valve 110 and/or outlet valve 120 is determined in response to the measured pressure successively increasing between respective pressure measurements performed during the repetitive squeezing-measuring-releasing cycle. For some applications, controller 180 may generate a signal indicative of the delayed closing of the valve.

As seen, if the inlet valve and/or the outlet valve is delayed in closing off confined section 152 of infusion line 150 when squeezing element 130 is raised, a vacuum can be created in the tube (i.e., suction may occur and a pressure may be measured that is lower than the pressure measured following the previous release of pressure). This is depicted by the successively decreasing valleys occurring at times t3, t5, and t7 for curve 506 of graph 500. Thus, for some applications, valve dysfunction may be determined in response to a vacuum being detected during the repetitive squeezing-measuring-releasing of the at least one round of valve operation check.

After verifying that the valves have closed off confined section 152 of infusion line 150 properly, the delivery session may be initiated. At that point, once proper closing of the valves is determined, any lack of pressure increase due to squeezing of confined section 152, measured during the air detection phase, is considered to be indicative of air in infusion line 150.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

Unless specifically stated otherwise, as apparent from the following discussions, it is appreciated that throughout the specification discussions utilizing terms such as "processing", "computing", "calculating", "determining", "estimating" "identifying, or the like, may refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses (e.g., processing circuits) for performing the operations herein. These apparatuses may be specially constructed for the desired purposes, or may comprise a general-purpose computer selectively activated or reconfigured by a computer program stored in the computer. Such a computer program may be stored in a computer readable storage medium, such as, but not limited to, any type of read-only memories (ROMs), random access memories (RAMs), electrically programmable read-only memories (EPROMs), electrically erasable and programmable read only memories (EEPROMs), or any other type of media suitable for storing electronic instructions, and capable of being coupled to a computer system bus.

The processes and displays presented herein are not inherently related to any particular computer or other apparatus. Various general-purpose systems may be used with programs in accordance with the teachings herein, or it may prove convenient to construct a more specialized apparatus to perform the desired method. The desired structure for a variety of these systems will appear from the description above. In addition, embodiments of the present invention are not described with reference to any particular programming language. It will be appreciated that a variety of programming languages may be used to implement the teachings of the inventions as described herein.

The invention may be described in the general context of computer-executable instructions, such as program modules, being executed by a computer. Generally, program modules include routines, programs, objects, components, data structures, and so forth, which perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. An infusion pump comprising:
   an inlet valve;
   an outlet valve;
   a squeezing element located between the inlet valve and the outlet valve and configured to squeeze a fluid line coupled to the infusion pump;
   a pressure sensor; and
   electric circuitry configured to:
   (i) perform at least one round of valve operation check prior to initiation of a delivery session of fluid to a subject, and
   (ii) subsequently, after an intake phase and before a delivery phase of at least one infusion pump cycle, determine, for the at least one infusion pump cycle, an absolute amount of air in the fluid line,
   wherein the at least one round of valve operation check and the determining of the amount of air in the fluid line each comprise the electric circuitry performing the steps of:
   (A) triggering closing the inlet valve to confine a section of the fluid line between the inlet valve and the outlet valve;
   (B) triggering squeezing, utilizing the squeezing element, of the confined section of the fluid line;
   (C) measuring the pressure within the confined section of the fluid line; and
   (D) subsequently, triggering relieving of the pressure in the confined section of the fluid line.

2. The infusion pump according to claim 1, wherein the electric circuitry is configured to trigger the squeezing of the confined section of the fluid line by moving the squeezing element from a Release position of the squeezing element toward a Squeeze position of the squeezing element, and wherein the electric circuitry is configured to measure the pressure by measuring the pressure while the squeezing element is positioned at a position that is between the Squeeze position of the squeezing element and the Release position of the squeezing element.

3. The infusion pump according to claim 2, wherein the electric circuitry is configured to trigger the relieving of the pressure in the confined section of the fluid line by raising the squeezing element, while the inlet valve and the outlet valve remain closed.

4. The infusion pump according to claim 2, wherein the electric circuitry is configured to trigger the relieving of the pressure in the confined section of the fluid line by raising the outlet valve, while (a) the squeezing element remains in the position that is between the Squeeze position of the squeezing element and the Release position of the squeezing element, and (b) the inlet valve remains closed.

5. The infusion pump according to claim 2, wherein the electric circuitry is configured to trigger the relieving of the pressure in the confined section of the fluid line by direct entry into the delivery stage of the delivery cycle, by raising the outlet valve simultaneously with lowering the squeezing element, while the inlet valve remains closed.

6. The infusion pump according to claim 1, wherein the measured pressure is indicative of a relative air content in the fluid delivered during the at least one infusion pump cycle, and wherein the electric circuitry is configured to determine the absolute amount of air by calculating a volume of air, based on (a) the delivered volume of fluid during the at least one infusion pump cycle and (b) the relative air content in the fluid delivered during the at least one infusion pump cycle.

7. The infusion pump according to claim 6, wherein the electric circuitry is configured to repetitively trigger the squeezing and measure the pressure after the respective intake phase and before the respective delivery phase of each of a respective number of successive infusion pump cycles.

8. The infusion pump according to claim 7, wherein the electric circuitry is further configured to determine an accumulated amount of air based on the absolute amount of air determined for each of the respective infusion pump cycles.

9. The infusion pump according to claim 8, wherein the electric circuitry is further configured to enter the delivery phase by raising the outlet valve only when the accumulated amount of air in the fluid line is below a predetermined threshold value.

10. The infusion pump according to claim 8, wherein the electric circuitry is further configured to provide a signal in response to the accumulated amount of air in the fluid line being above a predetermined threshold value.

11. The infusion pump according to claim 1, wherein the electric circuitry is further configured to, in response to the at least one round of valve operation check, determine valve dysfunction of at least one valve selected from the group consisting of: the inlet valve and the outlet valve, wherein valve dysfunction comprises delayed closing of the selected valve, delayed opening of the selected valve, or the selected valve being stuck in either an open or closed position.

12. The infusion pump according to claim 11, wherein the electric circuitry is further configured to provide a signal indicative of the valve dysfunction.

13. The infusion pump according to claim 11, wherein the electric circuitry is further configured to determine valve dysfunction in response to the pressure measured during the at least one round of valve operation check being below a predetermined threshold value.

14. The infusion pump according to claim 1, wherein the pressure sensor comprises at least one sensor selected from the group consisting of: a piezoelectric sensor, a gauge pressure sensor, an optical sensor, and a proximity sensor.

* * * * *